US008604897B1

(12) United States Patent
Bratkovski et al.

(10) Patent No.: US 8,604,897 B1
(45) Date of Patent: Dec. 10, 2013

(54) METAMATERIAL-BASED DEVICES AND METHODS FOR FABRICATING THE SAME

(75) Inventors: Alexandre Bratkovski, Mountain View, CA (US); Wei Wu, Mountain View, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1556 days.

(21) Appl. No.: 11/881,287

(22) Filed: Jul. 26, 2007

(51) Int. Cl.
*H01P 7/10* (2006.01)
*G01N 22/00* (2006.01)

(52) U.S. Cl.
USPC ..... 333/219.1; 333/219; 333/227; 422/82.11; 422/82.05

(58) Field of Classification Search
USPC ........................ 356/300–334, 445; 250/336.1, 250/338.1–338.5, 339.01, 339.02; 977/953–960
See application file for complete search history.

(56) References Cited

U.S. PATENT DOCUMENTS

2006/0119853 A1* 6/2006 Baumberg et al. ............ 356/445

OTHER PUBLICATIONS

Loncar et al., Chemical sensors based on photonic crystal nanolasers, Laser Applications to Chemical and Environmental Analysis, Technical Digest (Optical Society of America, 2004), paper MB5.*
Psaltis et al., Developing optofluidic technology through the fusion of microfluidics and optics, Jul. 26, 2006, Nature 442, pp. 381-386.*
Wu et al., Optical metamaterials at near and mid-IR range fabricated by nanoprint lithography, Appl. Phys. A 87, Feb. 2007, p. 143-150.*
Wu et al., Discussion of the mechanism of extraordinary optical transmission in metallic gratings, International Symposium on Metamaterials 2006, p. 296-299.*
Ueda et al., Composite right/left handed metamaterial structures composed of dielectric resonators and parallel mesh plates, Microwave Symposium, Jun. 2-8, 2007, IEEE/MTT-S International, p. 1823-1826.*
Zhang et al., Experimental Demonstration of Near-Infrared Negative-Index Metamaterials, Sep. 23, 2005, American Physical Society, Phys. Rev. Lett., 95(13), p. 137404-1-137404-4.*
Shuang Zhang, Wenjun Fan, Kevin J. Malloy, Steven R. J. Brueck, Nicolae C. Panoiu, and Richard M. Osgood, "Demonstration of metal-dielectric negative-index metamaterials with improved performance at optical frequencies," J. Opt. Soc. Am. B 23, 434-438 (2006).*

* cited by examiner

*Primary Examiner* — In Suk Bullock
*Assistant Examiner* — Robert Eom

(57) ABSTRACT

Various embodiments of the present invention are directed to metamaterial-based devices and to methods of fabricating metamaterial-based devices. In one embodiment, a metamaterial-based device comprises a channel layer, a top metallic layer, and a bottom metallic layer. The channel layer has a top and a bottom surfaces, and at least one channel configured to transmit at least one material. The top metallic layer has a top surface and a bottom surface attached to the top surface of the channel layer and has a first lattice of openings extending between the top and bottom surfaces of the top metallic layer. The bottom metallic layer has a top surface and a bottom surface, wherein the top surface of the bottom metallic layer is attached to the bottom surface of the channel layer.

19 Claims, 16 Drawing Sheets

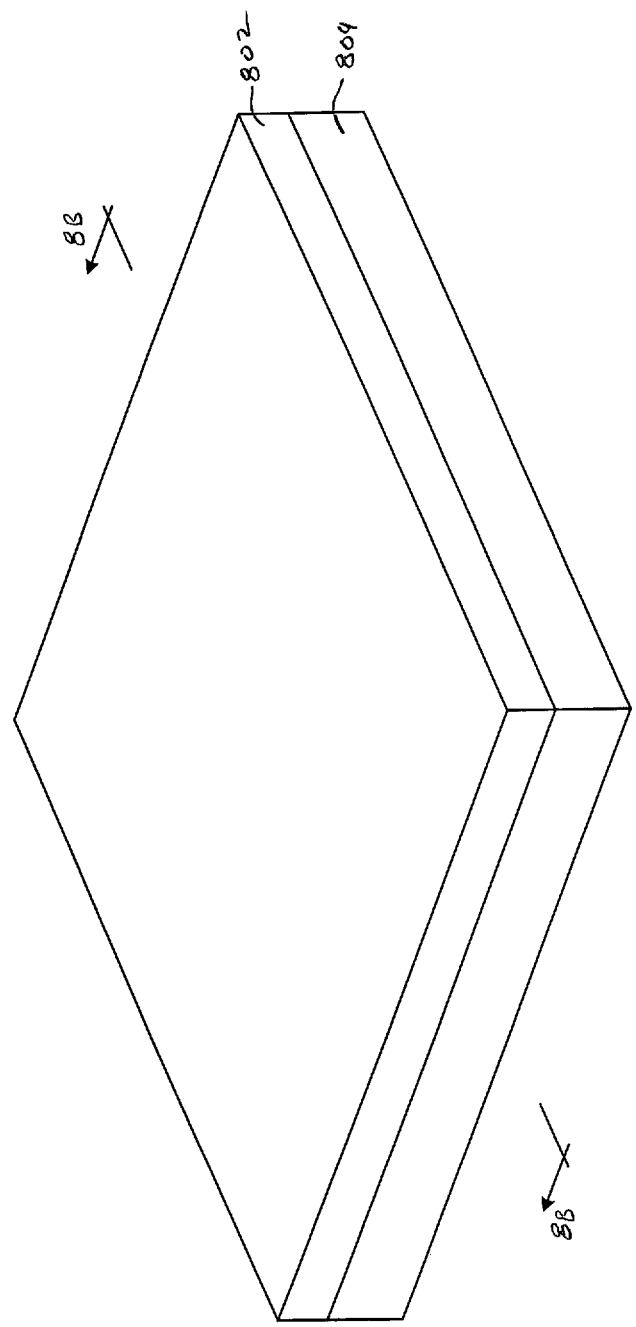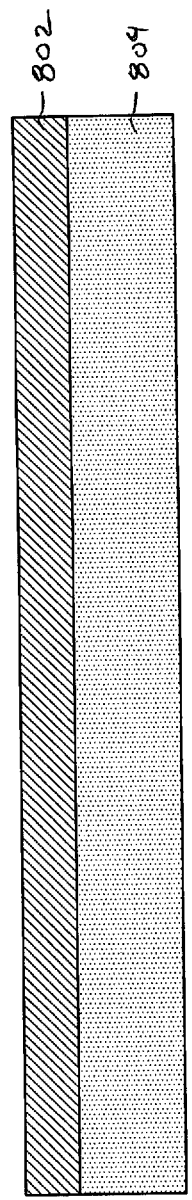
Figure 8A
Figure 8B

METAMATERIAL-BASED DEVICES AND METHODS FOR FABRICATING THE SAME

TECHNICAL FIELD

Embodiments of the present invention relate to metamaterial-based devices, and, in particular, to metamaterial-based devices that can be used in chemical sensors that can be included in lab-on-a-chip devices.

BACKGROUND

Analyte detection technology is currently employed in a wide range of disciplines ranging from electrochemical analysis through measurements to detect the presence and amount of biological compounds to pollution monitoring and industrial control. For example, chemical sensors have been developed to determine carbon dioxide levels in underground parking structures and in industrial manufacturing plants and to detect the presence of certain toxic chemicals in homes and in mines. Federal, state, and local governments have become increasingly aware of the dangers posed by many airborne pollutants and have begun to regularly monitor the levels of pollutants using chemical sensors. In addition, the threat of terrorist attacks employing toxic chemical weapons has created public concern and a demand for chemical sensors that can detect particular chemical weapons so that government authorities can respond accordingly. In the medical fields sensors have also been developed to detect quantities of certain biological compounds.

Although advancements in engineering and scientific disciplines have made it possible to fabricate chemical sensors to detect a variety of different analytes, a typical chemical sensor is often limited to detection of a single analyte or a small number of different kinds of analytes. In addition, a number of steps may be needed to prepare an analyte for detection. For example, certain chemical sensors employ a fluorescent material immobilized on an optical-fiber core. An analyte is detected by observing a color change that results from the fluorescent material reacting with the analyte. However, in order to detect a different analyte, the fluorescent material needs to be changed to one that fluoresces when reacted with the different analyte. Certain types of biosensors may employ active biological or biologically derived components which form chemical bonds with an analyte and hold the analyte in position for detection by a chemical sensor. An indirect approach is to use an enzyme that catalyzes a chemical reaction when an analyte is present to produce a product that can be detected by a chemical sensor. The presence of the product is assumed to confirm the existence of the analyte.

In recent years, Raman spectroscopic methods have also been developed to detect analytes. A typically analyte molecule has a unique Raman spectra that can be used to identify the analyte. For example, Raman spectra obtained from gas and liquid phase Raman scattering have been used to identify certain unknown analyte molecules. However, the intensities associated with these Raman spectra are often weak. In more recent years, surface-enhanced Raman spectroscopy ("SERS") has been developed as an analyte-detection tool. Raman scattering from an analyte adsorbed on or even within a few Angstroms of a metal surface can be $10^3$-$10^6$ times greater than Raman scattering observed for the same analyte in gas or liquid phases. SERS enhances the Raman spectra of an analyte via two mechanisms. The first mechanism is an enhanced electromagnetic field called a surface plasmon produced at the surface of a metal. The surface plasmon can be created when the wavelength associated with incident electromagnetic radiation is close to the plasma wavelength of the metal surface. Molecules adsorbed or in close proximity to the surface experience a larger electromagnetic field than the field used to produce the Raman scattering in the liquid and gas phase. The second mechanism of enhancement results from the formation of a charge-transfer complex between the metal surface and the analyte. However, even SERS is not able to provide the enhancement often needed to identify a wide variety of analytes.

SUMMARY

Various embodiments of the present invention are directed to metamaterial-based devices and to methods of fabricating metamaterial-based devices. In one embodiment of the present invention, a metamaterial-based device comprises a channel layer, a top metallic layer, and a bottom metallic layer. The channel layer has a top surface, a bottom surface, and at least one channel configured to transmit at least one material. The top metallic layer has a top surface and a bottom surface attached to the top surface of the channel layer and has a first lattice of openings extending from the top surface to the bottom surface of the top metallic layer. The bottom metallic layer has a top surface and a bottom surface, wherein the top surface of the bottom metallic layer is attached to the bottom surface of the channel layer.

BRIEF DESCRIPTION OF THE DRAWINGS

FIGS. 8A-8J show isometric and cross-sectional views that correspond to steps of a method for fabricating the metamaterial-based device, shown in FIG. 1, in accordance with embodiments of the present invention.

DETAILED DESCRIPTION

Various embodiments of the present invention are directed to metamaterial-based devices that can be used in chemical sensors and to methods for fabricating these devices. The term "metamaterial" refers to devices comprised of composite materials that are configured to have electromagnetic responses that are different from the materials comprising the devices. In other words, metamaterial-based devices of the present invention can be configured to exhibit responses to particular wavelength ranges of electromagnetic radiation that are different from responses exhibit by the materials comprising the devices. Metamaterial-based devices of the present invention can be used in chemical sensors to identify certain gaseous or liquid materials using Raman spectroscopic methods.

Figure 1A:
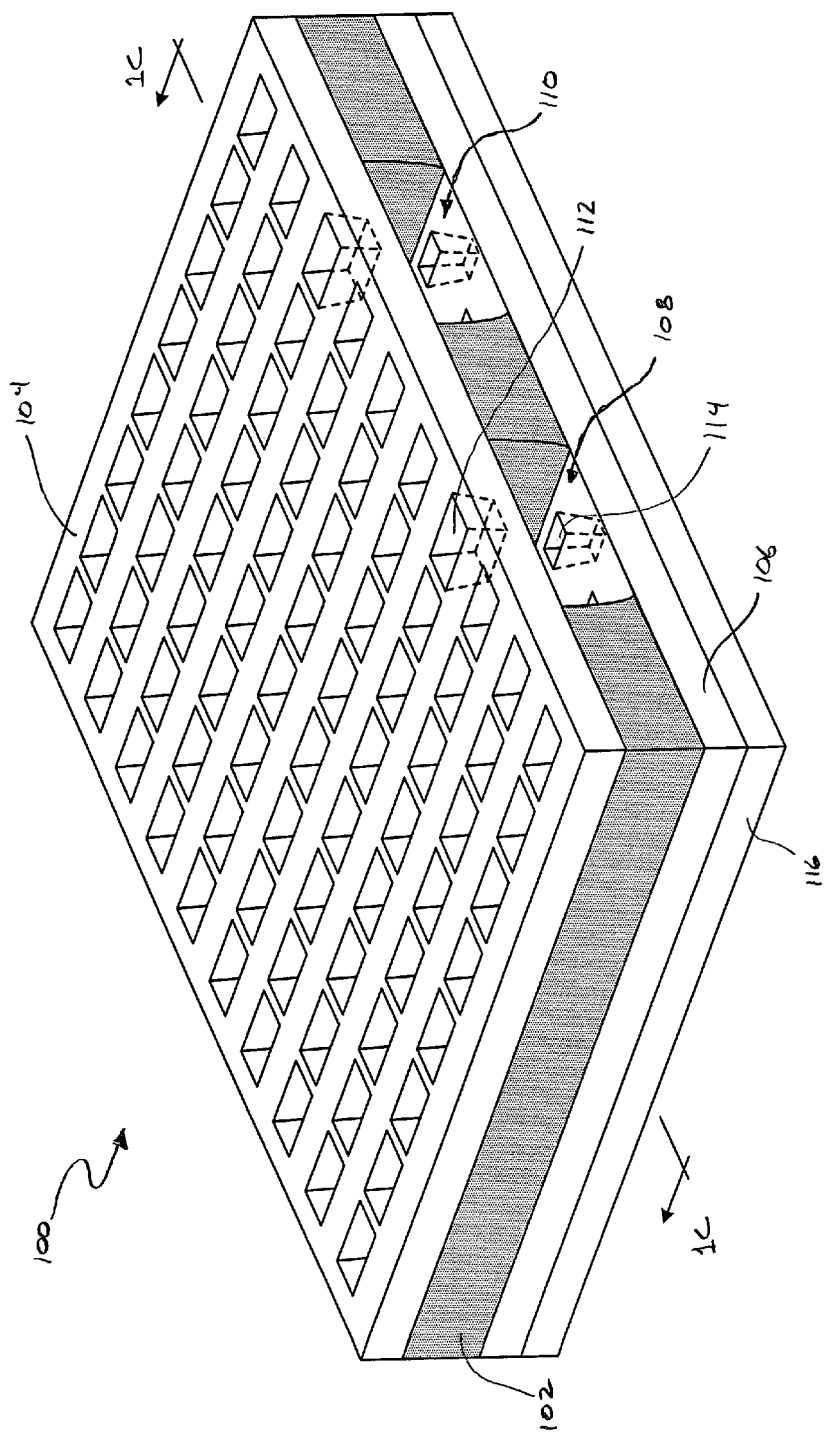
FIG. 1A shows an isometric view of a first metamaterial-based device in accordance with embodiments of the present invention.

FIG. 1A shows an isometric view of a first metamaterial-based device 100 in accordance with embodiments of the present invention. Metamaterial-based device 100 comprises a channel layer 102 sandwiched between a top-metallic layer 104 and a bottom-metallic layer 106. As shown in FIG. 1A, channel layer 102 includes two channels 108 and 110, which can be used to transmit material in either a gas or a liquid state. Top-metallic layer 104 and bottom-metallic layer 106 are "mesh-like" metallic structures. In other words, top-metallic layer 104 includes a lattice of tapered openings, such as tapered opening 112, that progressively narrow from the top surface to the bottom surface of top-metallic layer 104. Bottom-metallic layer 106 also includes a lattice of openings (shown in subsequent figures), such as opening 114, that progressively narrow from the top surface to the bottom surface of bottom-metallic layer 106. Metamaterial-based device 100 is supported by a dielectric substrate 116.

Figure 1B:
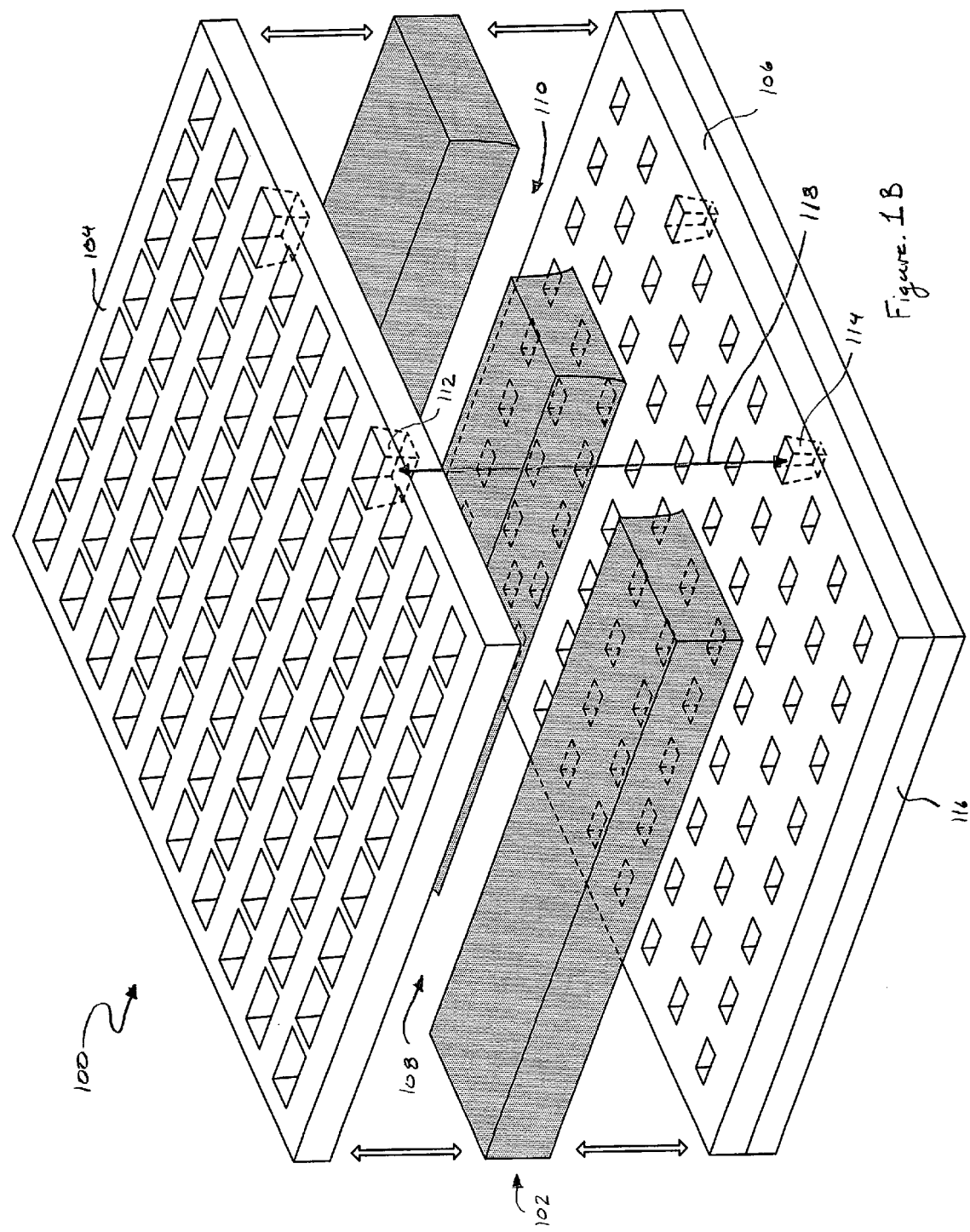
FIG. 1B shows an exploded isometric view of the first metamaterial-based device shown in FIG. 1A in accordance with embodiments of the present invention.

FIG. 1B shows an exploded isometric view of metamaterial-based device 100 in accordance with embodiments of the present invention. As shown in FIG. 1B, channels 108 and 110 span the width of channel layer 102 so that a material can be transmitted through channels 108 and 110. FIG. 1B also reveals the lattice of openings in bottom-metallic layer 106. The openings in top-metallic layer 104 are larger than the openings in bottom-metallic layer 106, and each opening in top-metallic layer 104 is substantially aligned with a corresponding opening in bottom-metallic layer 106. For example, double-headed arrow 118 indicates that opening 112 in top-metallic layer 104 is substantially aligned with opening 114 in bottom-metallic layer 106. Although, the tapered openings in metallic layers 104 and 106 are rectangular, in other embodiments of the present invention, the tapered openings can be square, circular, elliptical, irregularly shaped, or have any other suitable shape. In various embodiments of the present invention, metallic layers 104 and 106 can be comprised of silver, gold, aluminum, titanium, copper, or any other suitable metal or metal alloy that allows for the formation of plasmons, as described below with reference to FIGS. 5-6.

Figure 1C:
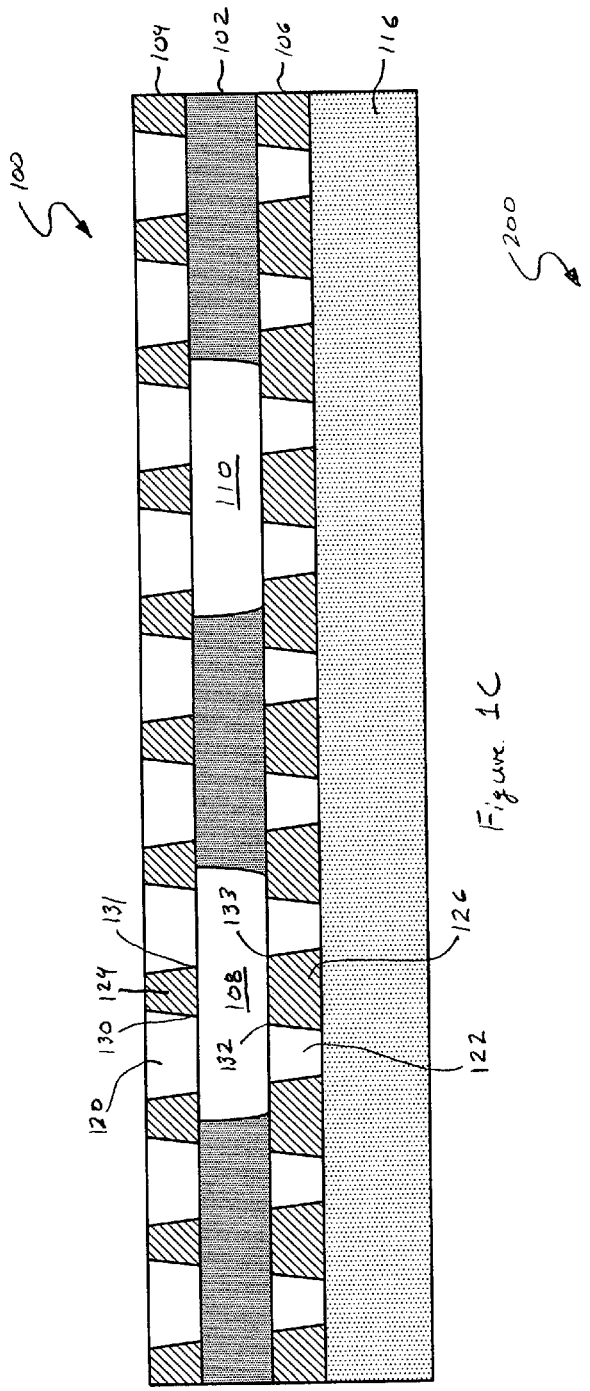
FIG. 1C shows a cross-sectional view of the first metamaterial-based device along a line 1C-1C, shown in FIG. 1A, in accordance with embodiments of the present invention.

FIG. 1C shows a cross-sectional view of metamaterial-based device 100 along a line 1C-1C, shown in FIG. 1A, in accordance with embodiments of the present invention. The openings in top-metallic layer 104 are located above the openings in bottom metallic layer 106. For example, an opening 120 in top-metallic layer 104 is located above an opening 122 in bottom-metallic layer 106. FIG. 1C reveals that the openings in metallic layers 104 and 106 taper toward substrate 116. Regions of top-metallic layer 104 between openings and regions between openings of bottom-metallic layer 106 are tapered away from substrate 116 and are located above one another. For example, a tapered region 124 in top-metallic layer 104 is located above a tapered region 126 in bottom-metallic layer 106. Channels 108 and 110 in channel layer 102 are configured and positioned between metallic layers 104 and 106 so that edges of the tapered regions can be exposed to materials transmitted in channels 108 and 110. For example, edges 130-133 of tapered regions 124 and 126 are exposed in channel 108.

Figure 1D:
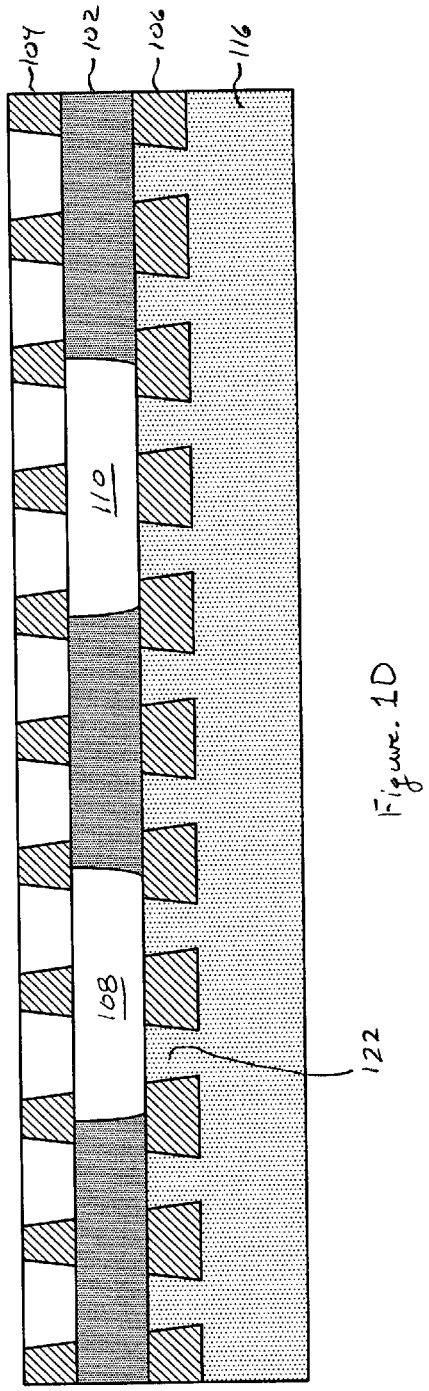
FIG. 1D shows a cross-sectional view of a second metamaterial-based device in accordance with embodiments of the present invention.

FIG. 1D shows a cross-sectional view of a second metamaterial-based device 200 in accordance with embodiments of the present invention. Metamaterial-based device 200 is identical to metamaterial-based device 100 except, as shown in FIG. 1D, the openings in the lattice of openings of bottom-metallic layer 106 are filled with the same material comprising substrate 116. For example, opening 122 is filled with the material comprising substrate 116.

Figure 2A:
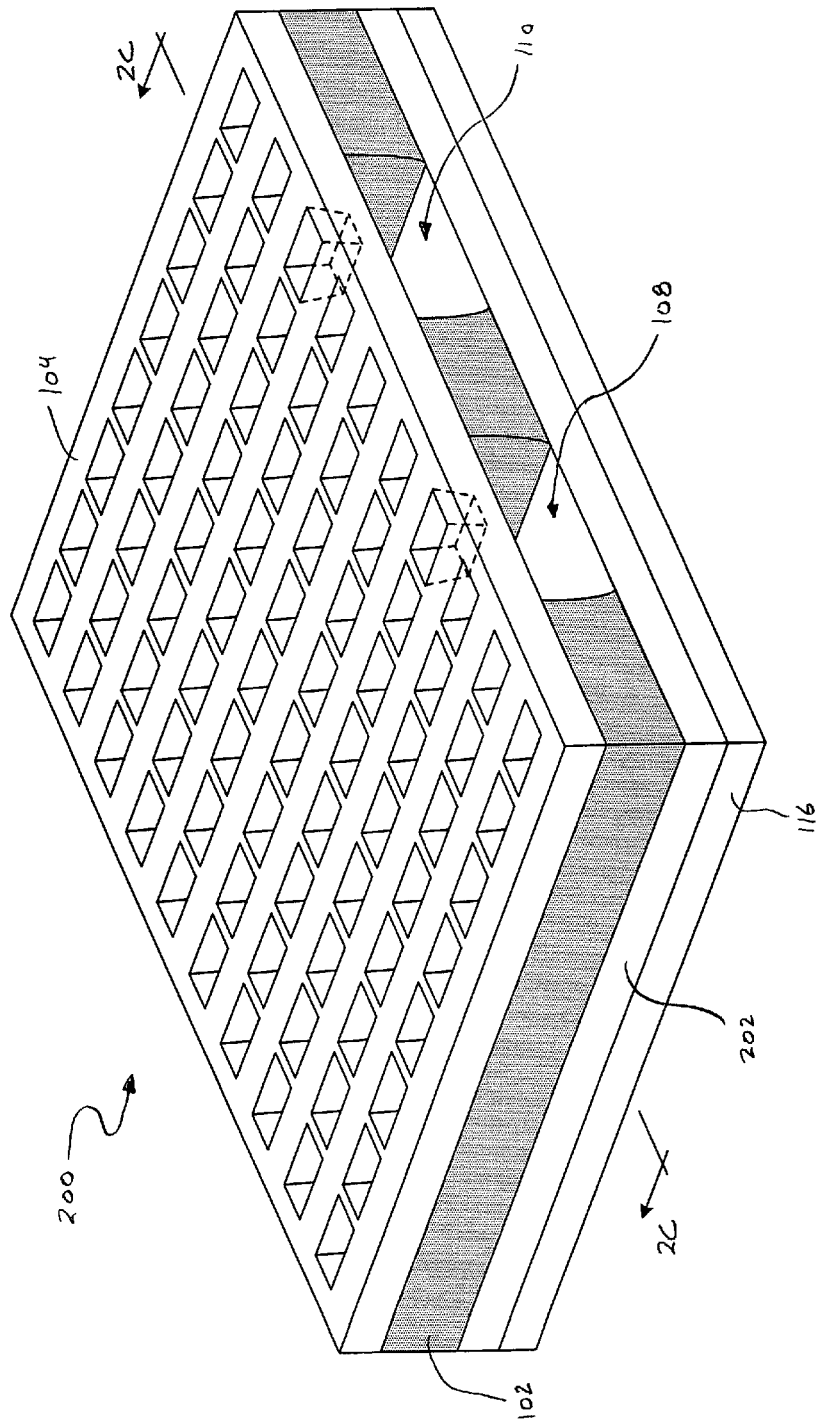
FIG. 2A shows an isometric view of a third metamaterial-based device in accordance with embodiments of the present invention.

FIG. 2A shows an isometric view of a third metamaterial-based device 200 in accordance with embodiments of the present invention. Metamaterial-based device 200 is substantially identical to metamaterial-based device 100 except bottom-metallic layer 106 of metamaterial-based device 100 has been replaced by a bottom-metallic layer 202 that does not include a lattice of openings.

Figure 2B:
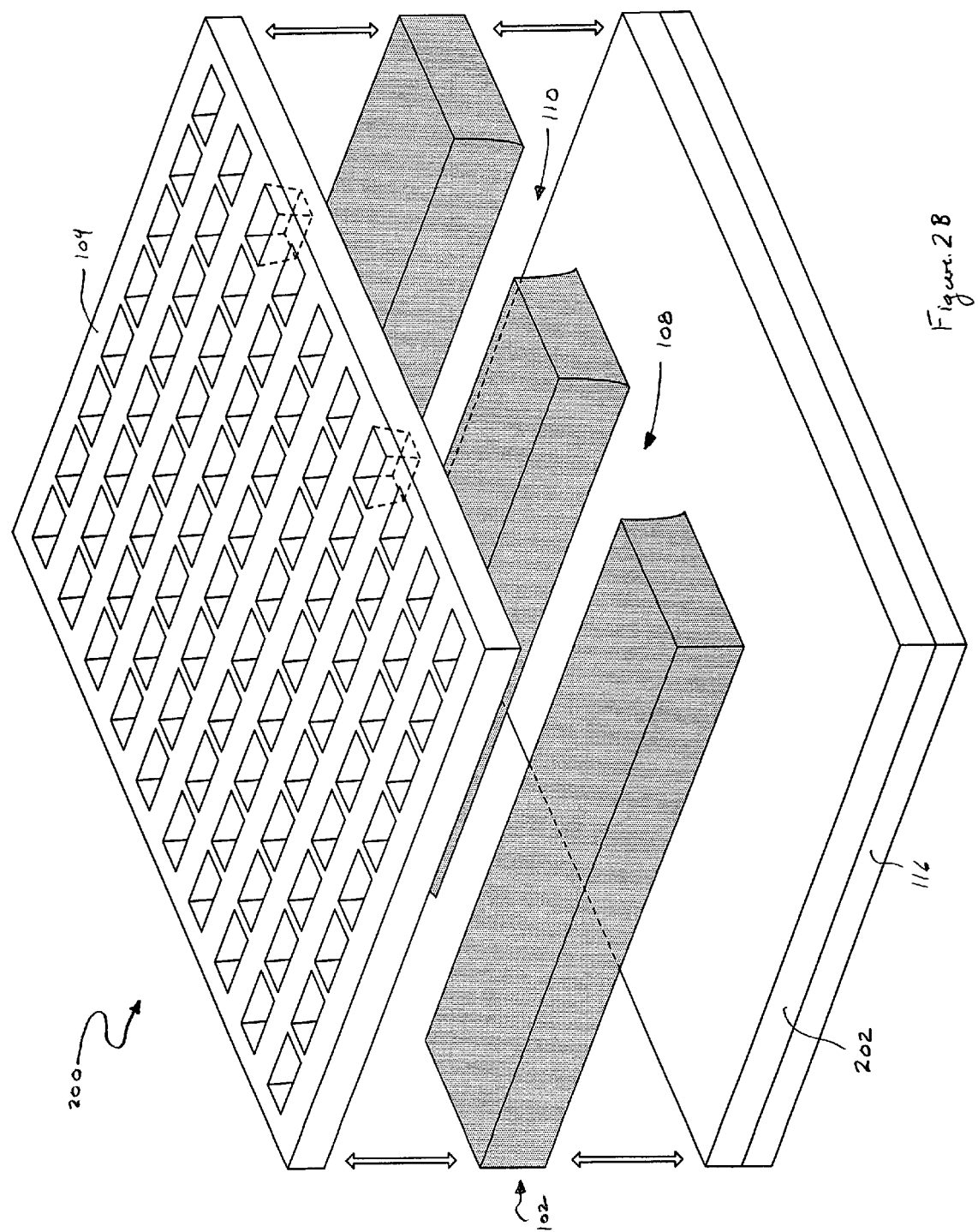
FIG. 2B shows an exploded isometric view of the third metamaterial-based device shown in FIG. 1A in accordance with embodiments of the present invention.

FIG. 2B shows an exploded isometric view of metamaterial-based device 200 in accordance with embodiments of the present invention. FIG. 2B reveals that unlike bottom-metallic layer 106 of metamaterial-base device 100, bottom-metallic layer 202 does not include a lattice of openings. Bottom metallic layer 202 can be comprised of silver, gold, titanium, copper, or any other suitable metal or metal alloy that allows for the formation of surface plasmons, as described below with reference to FIGS. 5-6.

Figure 2C:
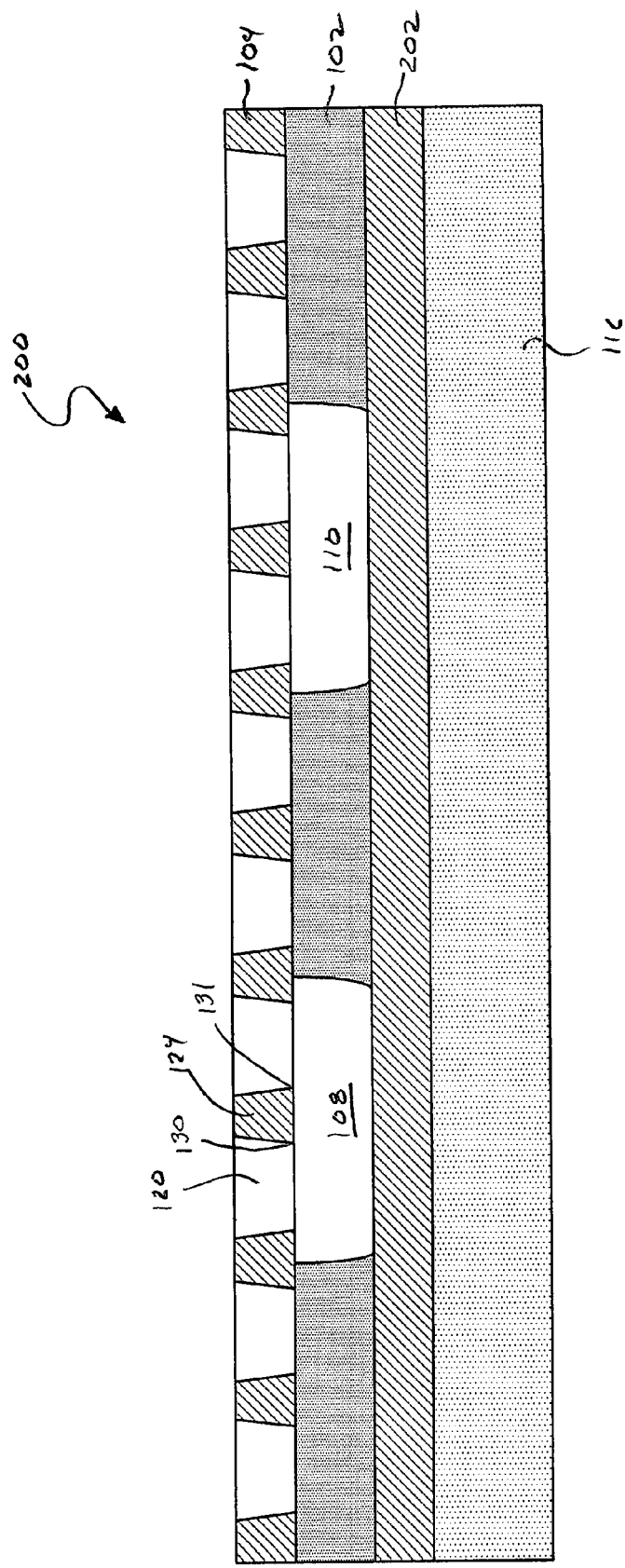
FIG. 2C shows a cross-sectional view of the third metamaterial-based device along a line 2C-2C, shown in FIG. 2A, in accordance with embodiments of the present invention.

FIG. 2C shows a cross-sectional view of metamaterial-based device 200 along a line 2C-2C, shown in FIG. 2A, in accordance with embodiments of the present invention. Channels 108 and 110 in channel layer 102 are configured and positioned between metallic layers 104 and 202 so that edges of the tapered regions can be exposed to materials transmitted in channels 108 and 110. For example, edges 130-131 of tapered region 124 are exposed in channel 108.

In other embodiments of the present invention, the sidewalls forming the regions between openings in metallic layers 104 and 106 can be substantially vertical. In other embodiments of the present invention, openings can taper away from substrate 116, and regions of metallic layers 104 and 106 between openings can taper toward substrate 116. In still other embodiments of the present invention, openings in metallic layer 104 can also be filled with a suitable dielectric material that seals metallic layer 104.

Figure 3A:
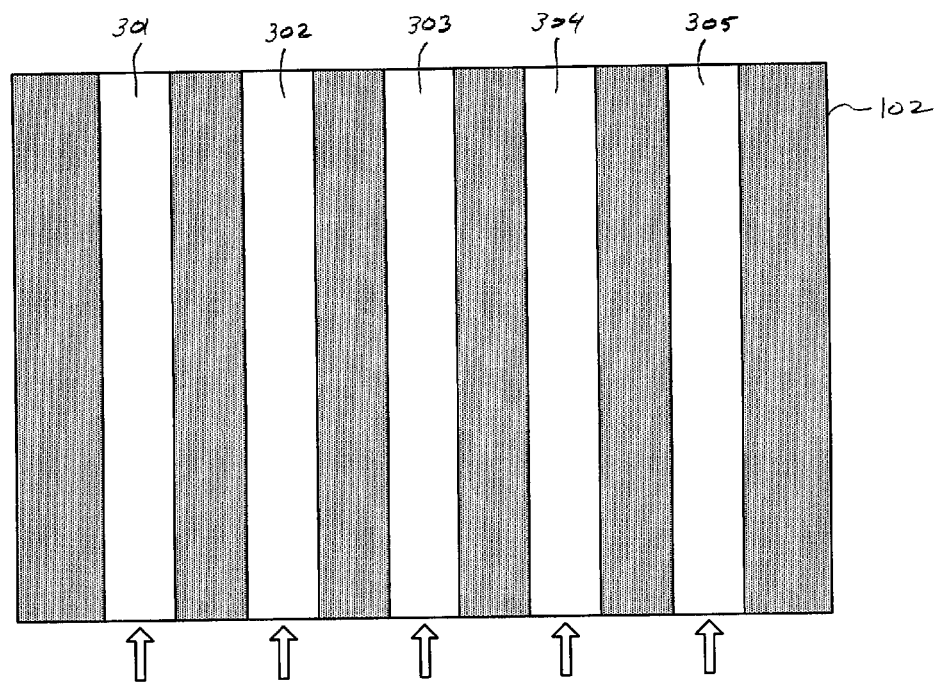
FIG. 3A shows a top view of a channel layer having five separate channels each which can be used to separately transmit a different material in accordance with embodiments of the present invention.
Figure 3B:
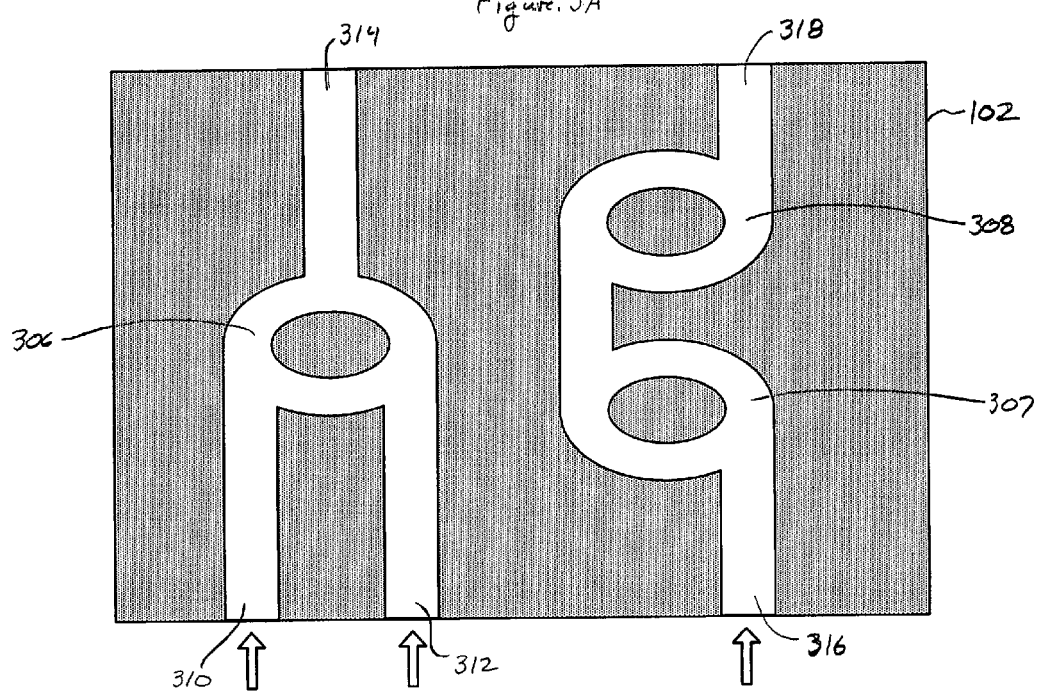
FIG. 3B shows a top view of a channel layer having three separate mixing chambers in accordance with embodiments of the present invention.

Channel layer 102 can be comprised of a group IV, a group III-V, a group II-VI semiconductor, $SiO_2$, $Si_3N_4$, a transparent polymer material, or a metal oxide. Channel layer 102 can also be configured with numerous channels, each of which can be used to transmit a different gaseous or liquid material. FIG. 3A shows a top view of channel layer 102 having five separate channels 301-305 that can each be used to separately transmit a different material in accordance with embodiments of the present invention. Channel layer 102 can also be configured with a number of mixing chambers for combining reacts to form products. FIG. 3B shows a top view of a channel layer 102 having 3 separate mixing chambers 306-308 for combining different reactants in accordance with embodiments of the present invention. Gaseous or liquid reacts can be introduced via separate channels 310 and 312 to form products in mixing chamber 306. The products formed in mixing chamber 306 exit channel layer 102 via channel 314. Gaseous or liquid reacts can be introduced one at a time via channel 316 to form products in mixing chambers 307 and 308. The products formed in mixing chambers 307 and 308 exit channel layer 102 via channel 318.

Figure 4A:
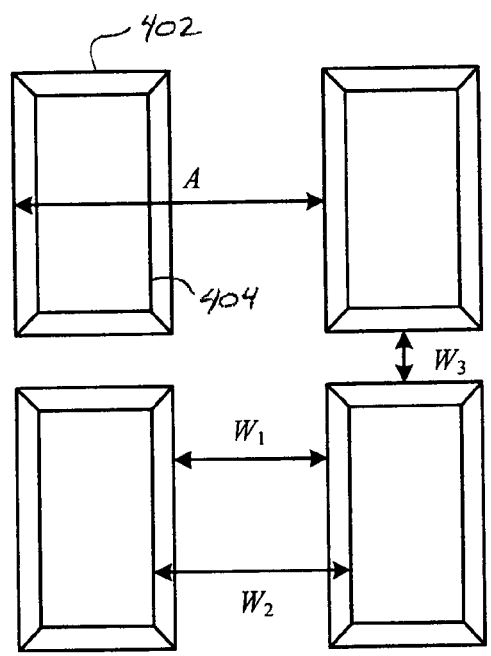
FIGS. 4A-4B show metamaterial-based-device parameters that can be varied in accordance with embodiments of the present invention.
Figure 4B:
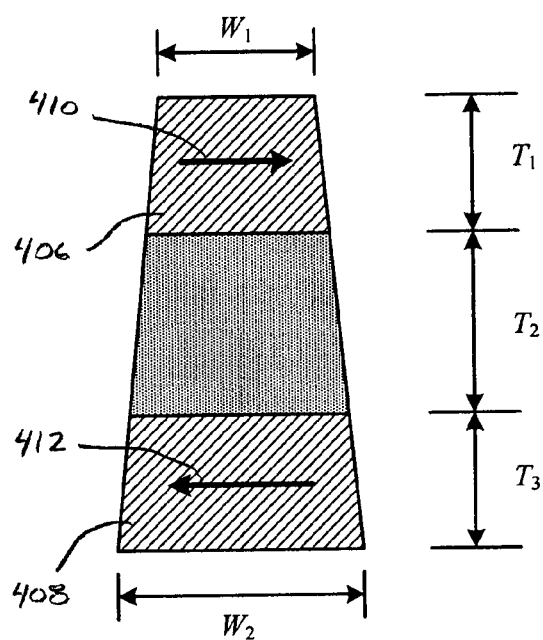

The thickness of the layers 102, 104, and 106, the size and aspect ratio of the openings, and the lattice constants associated with the lattice of openings can all be varied depending on the range of radiation wavelengths needed to produce a photonic interaction with metamaterial-based devices of the present invention. FIGS. 4A-4B show parameters associated with metamaterial-based device embodiments that can be varied in accordance with embodiments of the present invention. FIG. 4A shows parameters associated with a top view of four tapered openings. Outer rectangles, such as rectangle 402, represent the widest portion of each tapered opening, and inner rectangles, such as rectangle 404, represent the narrowest portion of each tapered opening. Parameter A represents the spacing between adjacent openings or the lattice constant, and parameters $W_1$, $W_2$, and $W_3$ represent widths between openings. FIG. 4B shows a cross-sectional view of a first tapered region 406 in top-metallic layer 104 and a second tapered region 408 in bottom-metallic layer 106. Parameters $T_1$, $T_2$, and $T_3$ represent thicknesses associated with top-metallic layer 104, channel layer 102, and bottom-metallic layer 106, respectively.

The parameters described above with reference to FIG. 4 can be varied so that devices of the present invention interact with certain wavelength ranges of incident electromagnetic radiation to exhibit negative effective permittivity $\epsilon_{eff}$, negative effective permeability $\mu_{eff}$, and a negative refractive index n. In other words, an electromagnetic wave propagating at a speed v=c/n, where c is the speed of electromagnetic radiation in vacuum, in metamaterial-based devices of the present invention propagates along a direction opposite the incident direction of the electromagnetic wave. The metallic regions of the metallic layers 104 and 106 produce a negative permeability and negative permittivity via a plasmonic response. The magnetic component of the electromagnetic radiation threading through openings induces current loops linking metallic regions of the metallic layers 104 and 106, as schematically represented by directional arrows 410 and 412 in FIG. 2B, resulting in $\mu_{eff}<0$.

Figure 5A:
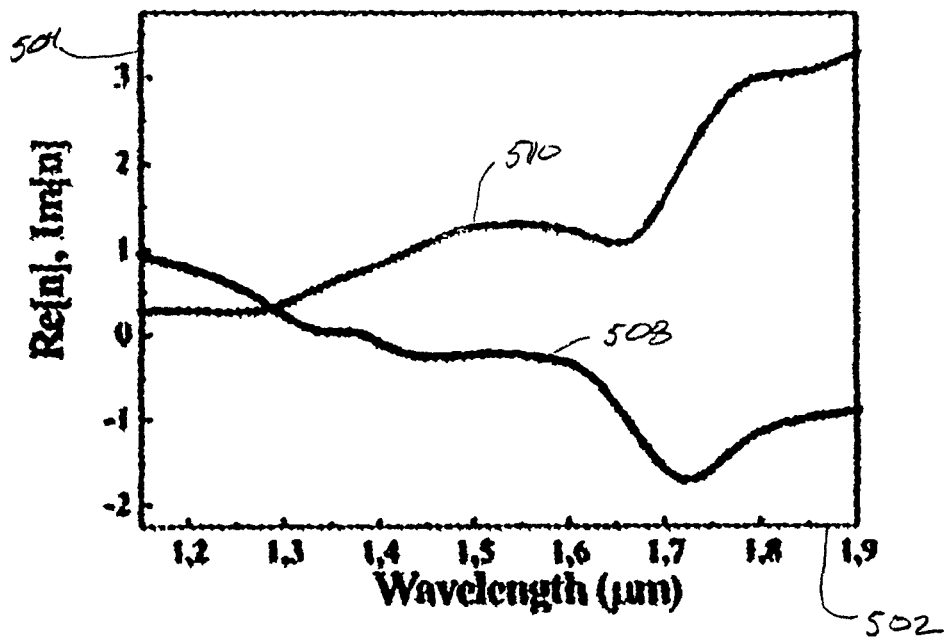
FIG. 5A shows a plot of real and imaginary components of a refractive index versus a range of wavelengths for an electromagnetic wave propagating through a hypothetical metamaterial-based device.
Figure 5B:
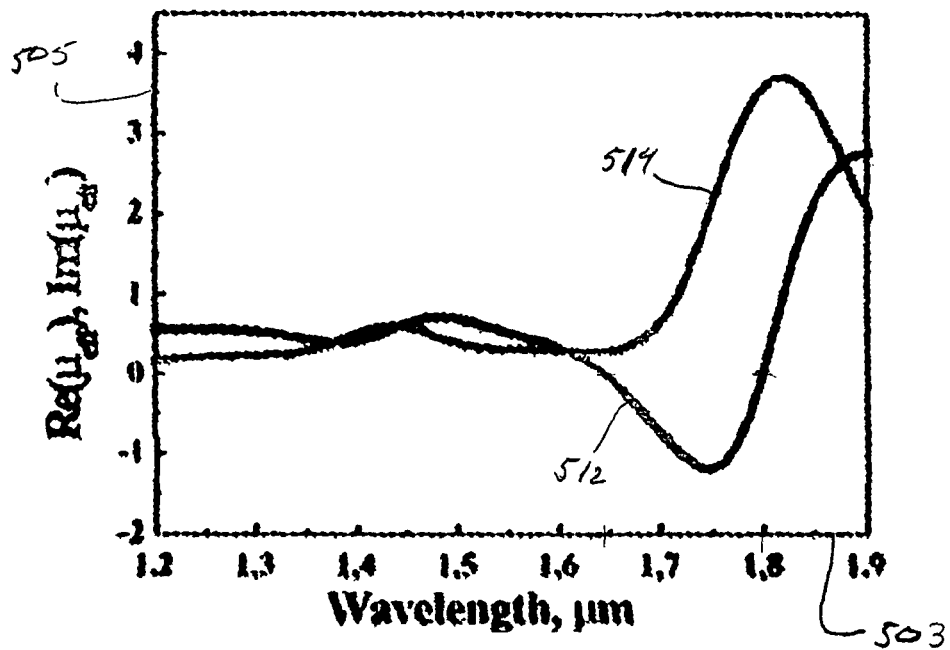
FIG. 5B shows a plot of real and imaginary components of the effective permeability versus a range of wavelengths for an electromagnetic wave propagating through a hypothetical metamaterial-based device.

A refractive index n and an effective permeability $\mu_{eff}$ obtained from simulating an electromagnetic wave propagating through a hypothetical metamaterial-based device in accordance with embodiments of the present invention are provided in FIGS. 5A-5B, respectively. Horizontal axes 502 and 503 represent a range of wavelengths associated with electromagnetic waves propagating through the hypothetical metamaterial-based device, and vertical axes 504 and 505 represent values of real and imaginary components of the refractive index n and the effective permeability $\mu_{eff}$. The parameters used for the simulation are displayed in Table 1:

TABLE 1

| Parameter | Length (nm) |
|---|---|
| A | 320 |
| $W_1$ | 110 |
| $W_2$ | 124 |
| $W_3$ | 218 |
| $T_1$ | 25 |
| $T_2$ | 80 |
| $T_3$ | 25 |

The simulation was performed using the well-known Finite Difference in Time Domain method ("FDTD") (for a detailed description of FDTD, see A. Taflove and S. C. Hagness, *Computational Electrodynamics*, 2nd Edition (Artech House, Boston, 2000).

FIG. 5A shows a plot of real and imaginary components of a refractive index n versus a range of wavelengths for an electromagnetic wave propagating through the hypothetical metamaterial-based device. Curve 508 represents the real component of n, Re[n], and curve 510 represents the imaginary component of n, Im[n]. Curve 508 is negative for electromagnetic waves with wavelengths greater than about 1.4 µam, and has the approximate value −1.7 at an approximate resonant wavelength 1.72 µm. Electromagnetic waves propagating through the hypothetical metamaterial-based device with wavelengths greater than about 1.4 µm experience a negative refractive index, and, as a result, have a negative angle of refraction.

A property of metamaterial-based device embodiments of the present invention is that incident electromagnetic waves having an appropriate wavelength create resonant electromagnetic surface waves, called "surface plasmons," which are localized along the surface and edges of metallic layers 104 and 106. Surface plasmons are formed along the surface of metallic objects when the real part of the effective permittivity and permeability is negative. Surface plasmons formed on metallic layers 104 and 106 can propagate on the surfaces and can be localized to openings in metallic layers 104 and 106. FIG. 5B shows a plot of real and imaginary components of the effective permeability $\mu_{eff}$ versus a range of wavelengths for the same hypothetical metamaterial-based device. A curve 512 represents the real component of $\mu_{eff}$, Re[$\mu_{eff}$], and a curve 514 represents the imaginary component of $\mu_{eff}$, Im[$\mu_{eff}$]. Curve 512 is negative for electromagnetic waves with wavelengths between about 1.65 µm to about 1.8 µm. This signifies the presence of an electromagnetic resonance whereby surface plasmons are formed at the surface of metallic layers 104 and 106 in this range of wavelengths of incident radiation, with strongly enhanced local electric field facilitating an enhanced Raman scattering.

Figure 6:
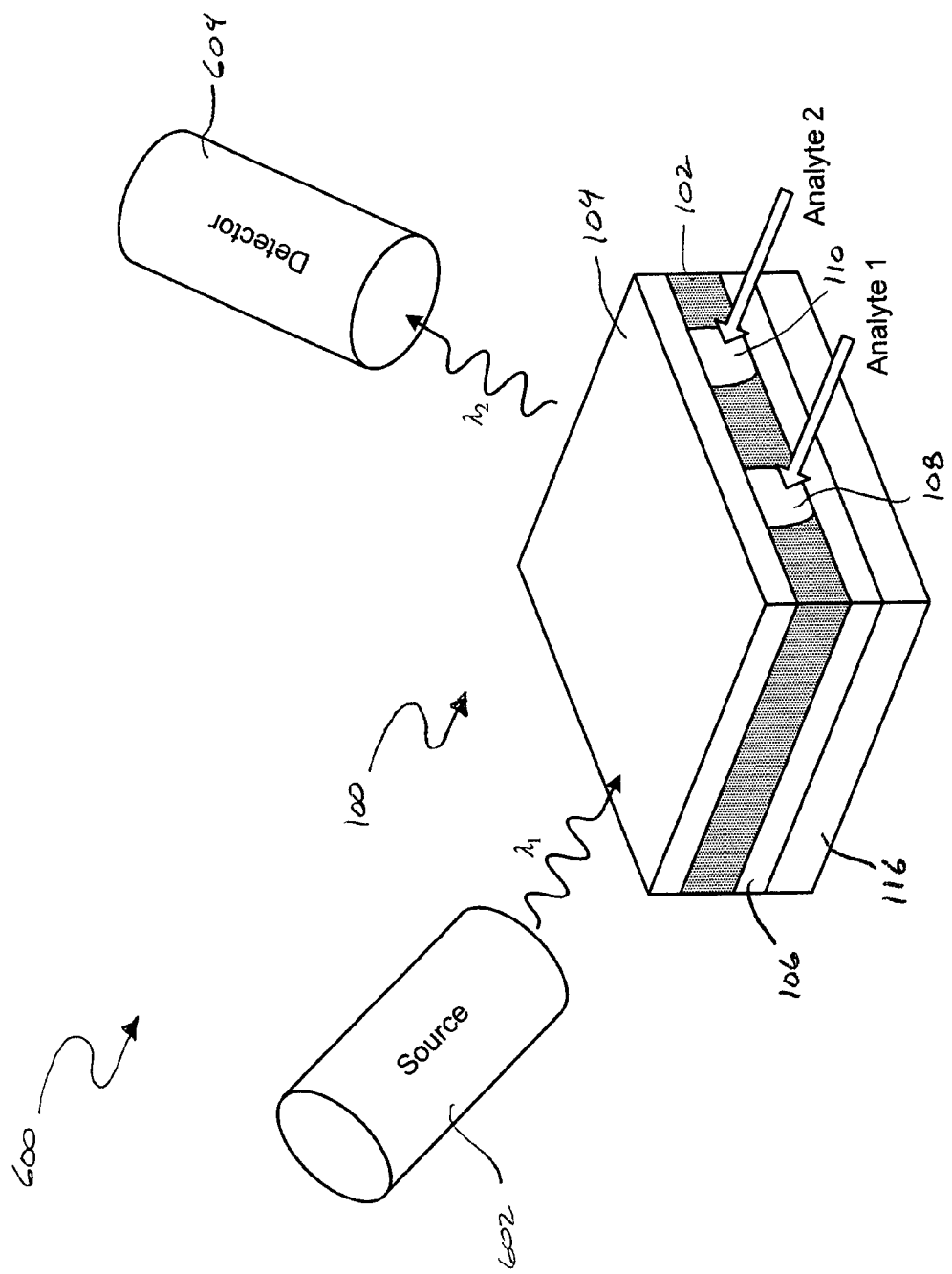
FIG. 6 shows a schematic representation of a chemical sensor that includes a metamaterial-based device in accordance with embodiments of the present invention.

Metamaterial-based devices of the present invention can be included in chemical sensors to intensify Raman scattering associated with Raman spectra that are used to identify unknown gaseous or liquid analytes transmitted via the channels of the channel layer. Raman spectra can also be used to identify products formed in mixing chambers of the channel layer. FIG. 6 shows a schematic representation of a chemical sensor 600 that includes metamaterial-based device 100 in accordance with embodiments of the present invention. Chemical sensor 600 also includes an electromagnetic radiation source 602 and a detector 604. Source 602 can be positioned so that emitted electromagnetic radiation is incident upon the metamaterial-based device 100 and can be configured to emit electromagnetic radiation with wavelengths that induce the formation of surface plasmons on metallic layers 104 and 106. The electric field of plasmons formed along the edges of the openings in the metallic layers 104 and 106 is considerably enhanced over those formed along surfaces. For example, referring to FIG. 1C, plasmon enhancement is strongest along edges 130-133 of metallic regions 124 and 126. Analytes 606 and 608 are injected into channels 108 and 110, respectively. The analyte molecules are attached to or are in close proximity to exposed surfaces and edges of metallic layers 104 and 106 along channels 108 and 110. The plasmon electric field component excites vibrational modes of the analyte molecules. Analyte molecules experience stronger plasmon electric field components along the edges of the openings than the plasmon electric field components formed along the surface of metallic layers 104 and 106. As a result, Raman scattering is enhanced for analytes molecules located close to the edges than for analyte molecules located on or close to surfaces of metallic layers 104 and 106. Detector 604 can be positioned and configured to detect electromagnetic radiation from analytes 606 and 608. In other embodiments of the present invention, metamaterial-based device 100 of chemical sensor 600 can be configured with mixing chambers, as described above with reference to FIG. 3, so that chemical sensor 600 can be used to detect formation of products. Note that, in other embodiments of the present invention, a chemical sensor substantially identical to chemical sensor 600 can include metamaterial-based device 200 rather than metamaterial-based device 100.

Figure 7:
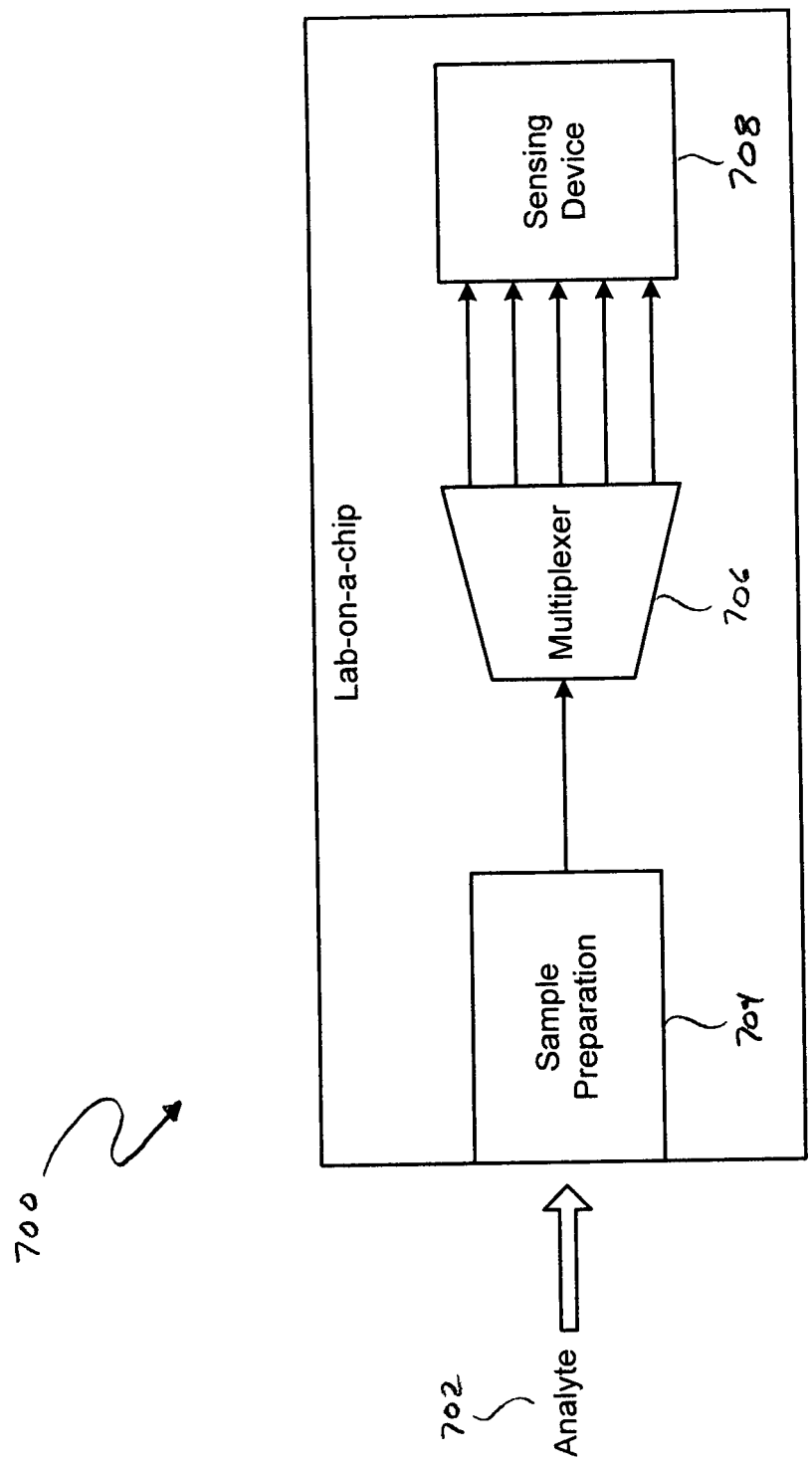
FIG. 7 shows a schematic representation of a lab-on-a-chip system that includes a chemical sensor in accordance with embodiments of the present invention.

Chemical sensor embodiments of the present invention can be included in lab-on-a-chip devices. Lab-on-a-chip devices integrate microfluidic systems on a microchip in order to automate many standard laboratory practices. Lab-on-a-chip devices may include a network of channels, mixers, reservoirs, and diffusion chambers that are etched into glass or a polymer chip and may also include integrated electrodes, pumps, valves, and other suitable miniature devices. FIG. 7 shows a schematic representation of a lab-on-a-chip device 700 that includes a chemical sensor in accordance with embodiments of the present invention. An unknown analyte 702 is injected into a sample preparation device 704, which may include an injector, dispenser, and preconcentrator. The prepared analyte is then transmitted to a multiplexer 706 that separates the analyte into components that are transmitted separately to a chemical sensor 708. Chemical sensor 708 can then be used to produce a Raman spectrum associated with each analyte.

Figure 8C:
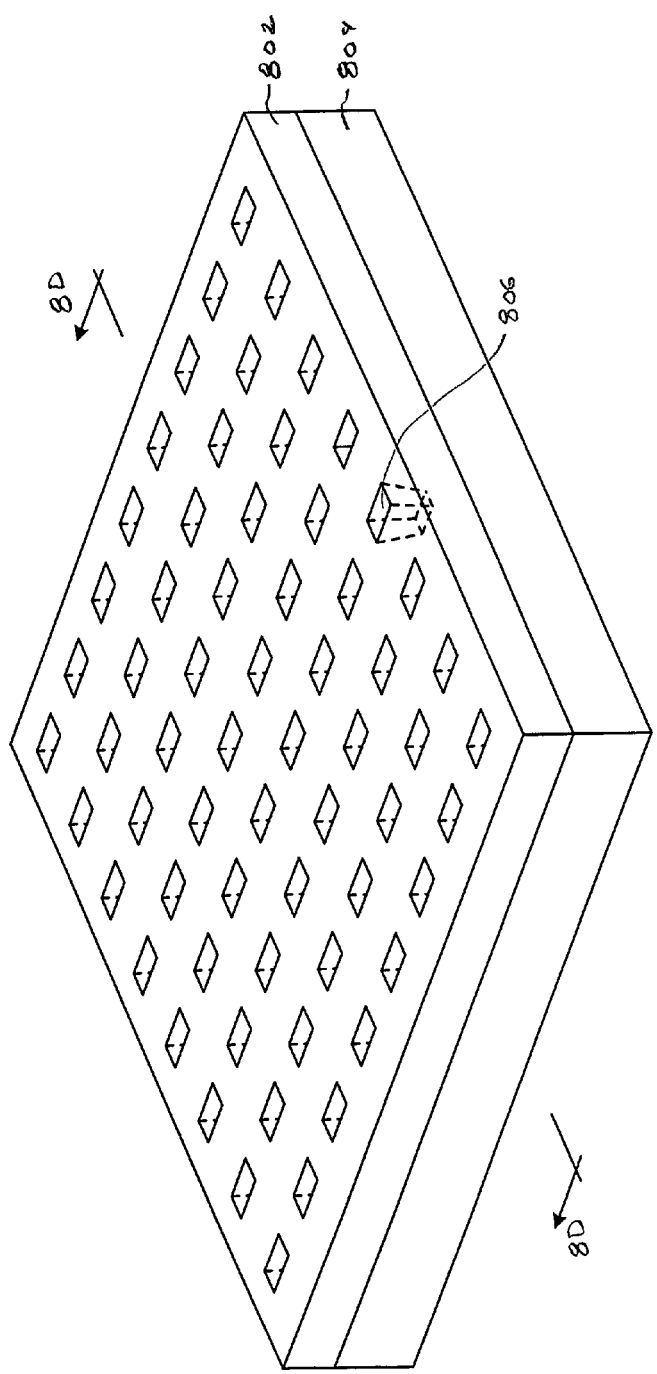

FIGS. 8A-8J show isometric and cross-sectional views that correspond to steps of a method for fabricating metamaterial-based device 100, shown in FIG. 1, in accordance with embodiments of the present invention. First, as shown in FIGS. 8A-8B, a bottom-metallic layer 802 is deposited on a substrate 804 using evaporation, sputtering, atom layer deposition ("ALD"), or wafer bonding. Bottom-metallic layer 802 can be comprised of silver, gold, aluminum, titanium, copper, or another suitable material, and substrate 804 can be comprised of $SiO_2$, $Si_3N_4$, or another suitable dielectric material.

Next, as shown in FIG. 8C, electron beam lithography ("EBL"), x-ray lithography, photolithography, focused ion beam lithography, extreme UV lithography ("EUVL"), or nanoimprint lithography ("NIL") can be used to form a lattice of openings, such as opening 806, in bottom-metallic layer 802. In other method embodiments of the present invention, a lift-off process can be used to form metallic layer 802 with the lattice openings. First, a resist is deposited on substrate 804 and patterned with crossing channels that correspond to the mesh-like structure shown in FIGS. 1-2 leaving pillars that correspond to openings in bottom-metallic layer 802 using any one of various lithography techniques. Second, silver, gold, aluminum, titanium, copper, or another suitable material is deposited over the resist and in the channels. Third, the resist is dissolved leaving bottom-metallic layer 802 with a lattice of openings. The openings in the lattice of openings can be rectangular, square, circular, elliptical, irregularly shaped, or another suitable shape, and the side walls of each opening can be tapered toward substrate 804, or substantially vertical. In an optional step of fabricating metamaterial-based device 100, as shown in a cross-sectional view of FIG. 8D, the lattice of openings in bottom-metallic layer 802 can be back filled with the same material comprising substrate 804 and the top surface of bottom-metallic layer 802 planarized. For example, region 808 is an opening in bottom-metallic layer 802 that has been back filled with substrate 804 material.

Figure 8D:
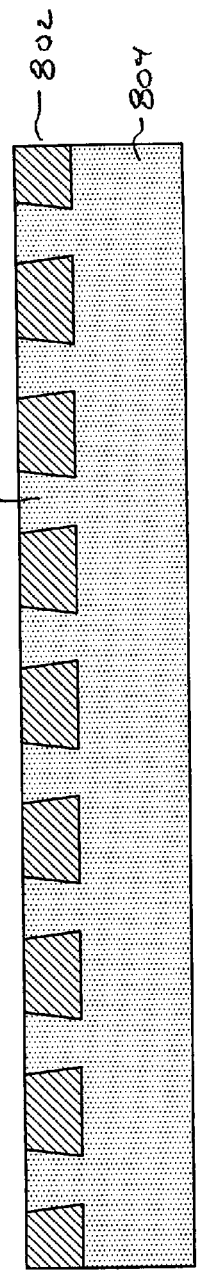

Note that the steps described with reference to FIGS. 8C and 8D are optional. For example, in other method embodiments of the present invention, forming the lattice of openings in bottom metallic layer 802 can be omitted in order to fabricate a metamaterial-based device with no lattice of openings in bottom metallic layer 802, such as bottom metallic layer 202 of metamaterial-base device 200 shown in FIG. 2.

Figure 8E:
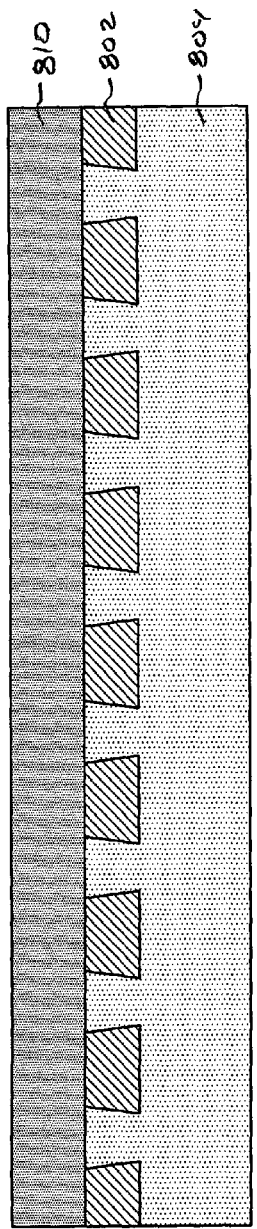
Figure 8F:
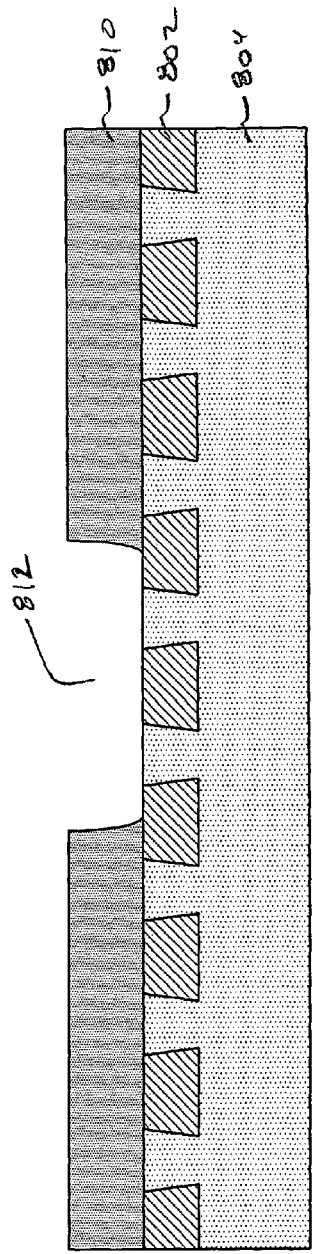
Figure 8G:
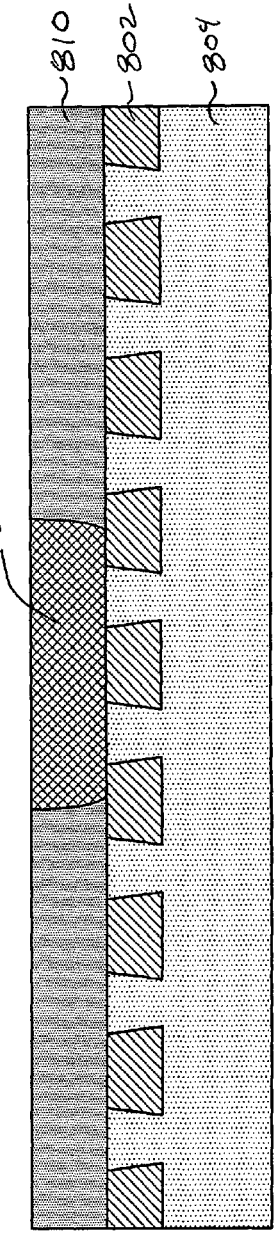

Next, in a cross-sectional view shown in FIG. 8E, a channel layer 810 is formed on the top surface of bottom-metallic layer 802 using CVD, MBE, ALD, evaporation, sputtering, or wafer bonding. The channel layer can be comprised of a group IV semiconductor, a group III-V semiconductor, a group II-VI semiconductor, polymers, or another suitable material. Next, in a cross-sectional view as shown in FIG. 8F, an opening 812 can be formed in channel layer 810 using electron beam lithography, nanoimprint lithography, reactive ion etching, chemically assisted ion etching, or focused ion beam milling, or in other embodiments, the lift-off process described above can be used. The opening 812 may represent a channel or a mixing chamber formed in channel layer 810. Next, in a cross-section view shown in FIG. 8G, opening 812 is filled with a polymer 814 using CVD spin-coating, or spray-coating and the surface can be planarized.

Figure 8H:
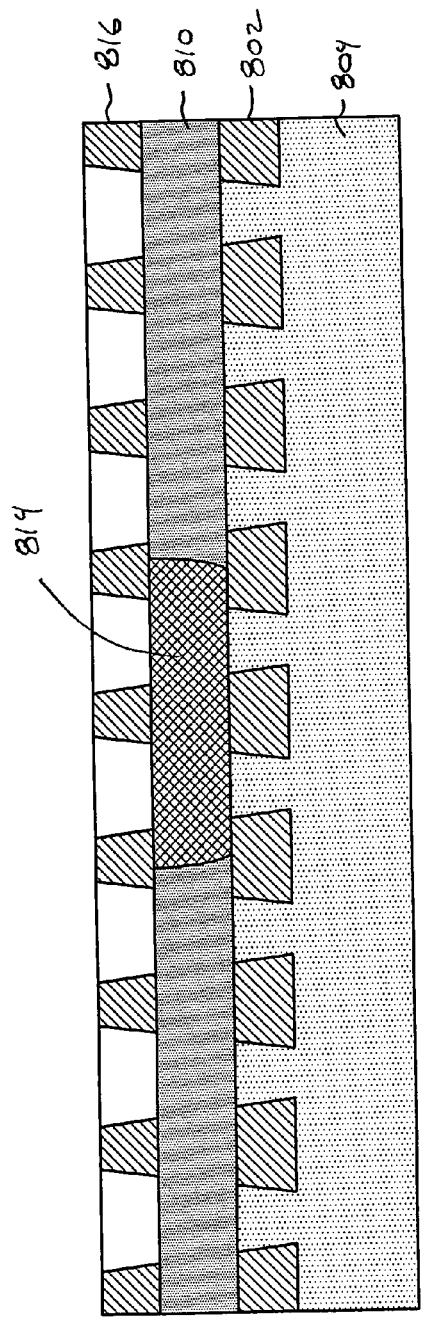
Figure 8I:
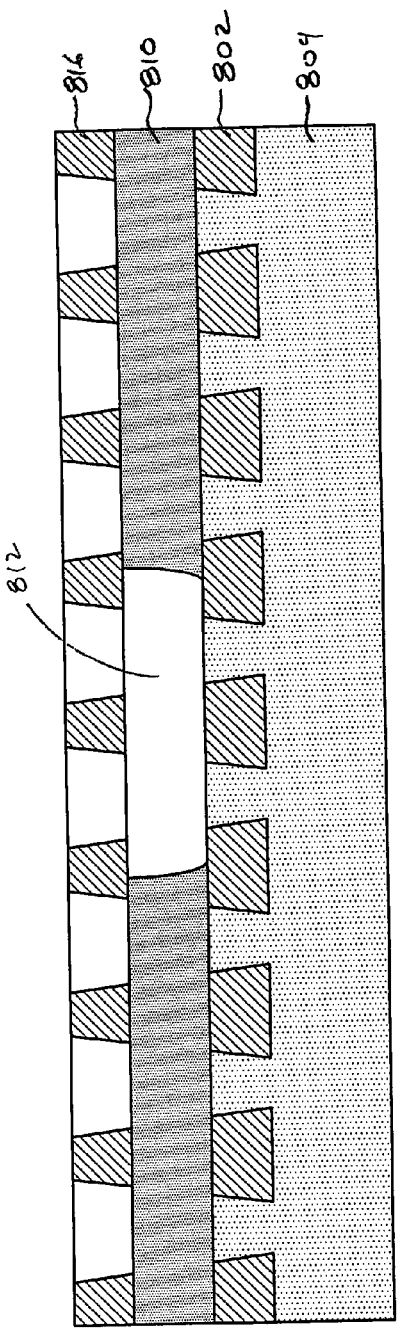
Figure 85:
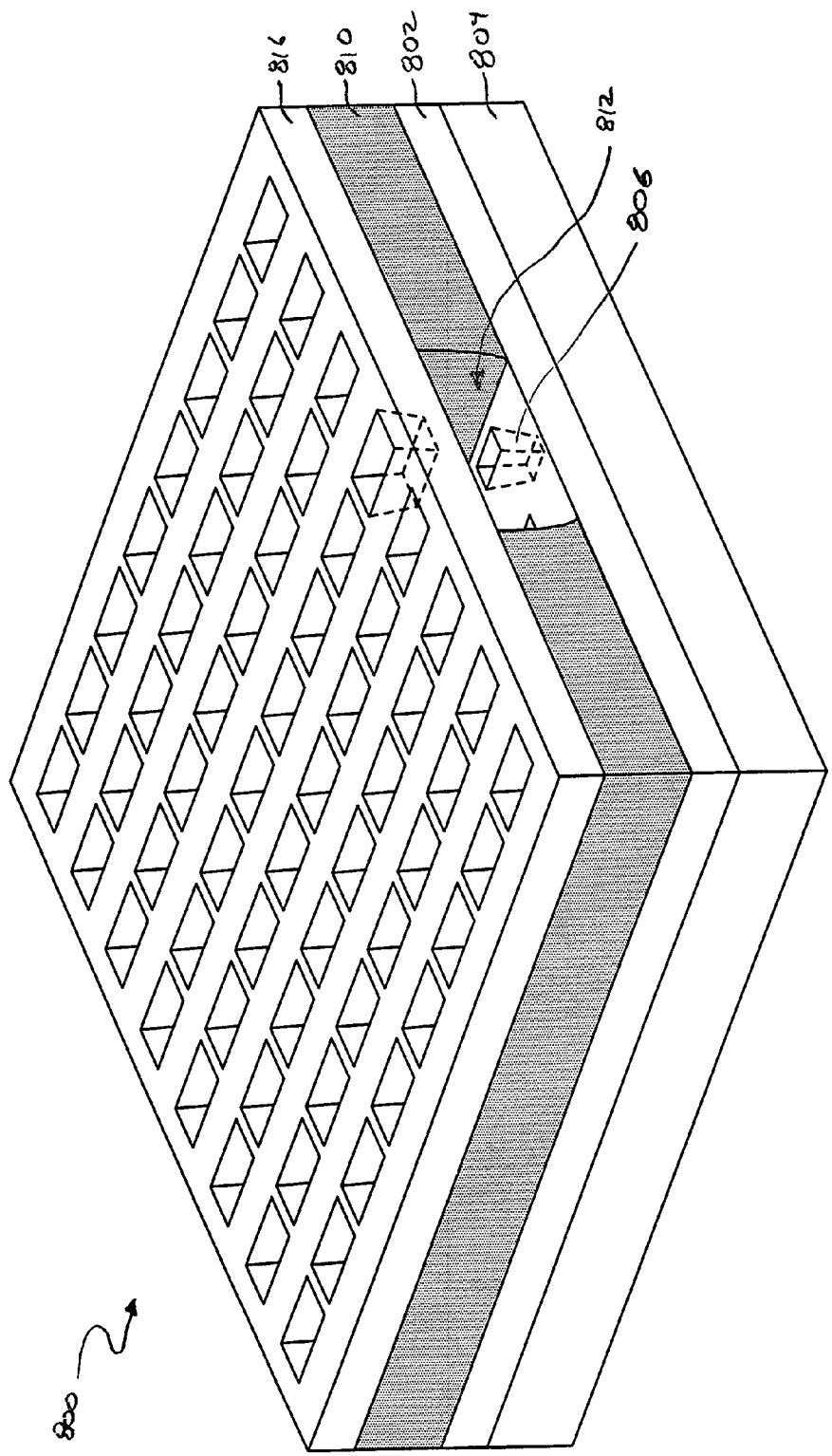

Next, in a cross-sectional view shown in FIG. 8H, a top-metallic layer 816 is deposited on channel layer 810 using evaporation, sputtering, ALD, or wafer bonding. EBL, x-ray lithography, photolithography, focused ion beam lithography, EUVL, or NIL can be used to form a lattice of openings in top-metallic layer 816. Top-metallic layer 816 can be comprised of silver, gold, aluminum, copper, or another suitable material. Next, in a cross-sectional view shown in FIG. 8I, polymer 814 is removed from opening 812 by applying an appropriate solvent that dissolves polymer 814. FIG. 8J shows an isometric view of a metamaterial-based device 800 fabricated in accordance with the steps described above with reference to FIGS. 8A-8I. In other method embodiments of the present invention, before the polymer 814 is removed from opening 812, a dielectric material can be deposited in the openings of the lattice of openings in metallic layer 816. In a subsequent, an appropriate solvent can then be used to dissolve polymer 814. As a result, openings in the lattice of openings in top metallic layer 816 are filled with dielectric material.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purposes of illustration and description. They are not intended to be exhaustive of or to limit the invention to the precise forms disclosed. Obviously, many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents:

The invention claimed is:

1. A metamaterial-based structure comprising:
a channel layer comprising a slab of channel layer material and having a channel to transmit a material from a first side to a second side of the structure, the channel to run parallel to a top surface of the channel layer and being bounded by sidewalls comprising the channel layer material to confine the material to be transmitted within the channel;
a top metallic layer attached to the top surface of the channel layer to cover the channel, the top metallic layer having a first lattice of openings with tapered sidewalls that extend from a top surface to a bottom surface of the top metallic layer; and
a bottom metallic layer attached to a bottom surface of the channel layer.

2. The structure of claim 1 wherein the bottom metallic layer further comprises a second lattice of openings that extend from a top surface to a bottom surface of the bottom metallic layer.

3. The structure of claim 2 wherein the second lattice of openings comprises an opening having tapered sidewalls, the tapered sidewalls of the opening in the second lattice to taper from the top surface to the bottom surface of the bottom metallic layer, and wherein an opening in the first lattice of openings is larger than and substantially aligned with an opening in the second lattice of openings.

4. The structure of claim 1 wherein the channel layer further comprises at least one mixing chamber coupled to the channel, wherein the material to be transmitted in the channel is to form at least one product in the at least one mixing chamber.

5. The structure of claim 1 wherein the channel layer material comprises one of:
a group IV semiconductor;
a III-V semiconductor;
a II-VI semiconductor; or
a polymer.

6. The structure of claim 1 wherein one or both the top metallic layer and the bottom metallic layer comprise one of:
silver;
gold;
aluminum;
titanium;
copper; or
alloys thereof.

7. The structure of claim 1 wherein an opening of the first lattice of openings opens into the channel in the channel layer to expose edges of the opening at the bottom surface of the top metallic layer to the material to be transmitted within the channel.

8. The structure of claim 7 further comprising a dielectric material to fill openings of the first lattice that open into the channel, the filled openings to further confine the transmitted material within the channel.

9. A chemical sensor comprising:
a metamaterial structure having a top metallic layer, a bottom metallic layer, and a channel layer sandwiched between the top metallic layer and the bottom metallic layer, the channel layer comprising a channel layer material and having at least one channel configured to transmit an analyte from a first side to a second side of the chemical sensor, the top metallic layer having a first lattice of openings with tapered sidewalls that extend from a top surface to a bottom surface of the top metallic layer, wherein the channel is parallel to a top surface of the channel layer and is bounded by sidewalls comprising the channel layer material to confine the transmitted analyte within the channel;
a source positioned to input electromagnetic radiation to the metamaterial structure, the electromagnetic radiation to induce surface plasmons on the top and bottom metallic layers that stimulates emission of output electromagnetic radiation from the analyte; and
a detector positioned to receive the output electromagnetic radiation emitted from the analyte.

10. The sensor of claim 9 wherein the metamaterial structure further comprises:
a second lattice of openings extending from a top surface to a bottom surface of the bottom metallic layer; and
a substrate having a top surface attached to a bottom surface of the bottom metallic layer.

11. The sensor of claim 10, wherein the openings in the second lattice of openings comprise tapered sidewalls.

12. The sensor of claim 9 wherein the channel layer further comprises at least one mixing chamber to combine the analyte transmitted in the channel.

13. The sensor of claim 9 wherein the channel layer material comprises one of:
a group IV semiconductor;
a III-V semiconductor;
a II-VI semiconductor;
$SiO_2$;
$Si_3N_4$; or
a metal oxide,
and wherein one or both of the top metallic layer and the bottom metallic layer comprise one of:
silver;
gold;
aluminum;
titanium;
copper; or
alloys thereof.

14. A method for fabricating a metamaterial-based structure, the method comprising:
forming a bottom metallic layer on a substrate;
forming a channel layer on the bottom metallic layer, the channel layer comprising a slab of channel layer material;
forming a channel in the channel layer across the slab of channel layer material parallel to the bottom metallic layer, the channel to transmit a material within the channel, the channel having sidewalls comprising the channel layer material to confine the material to be transmitted within the channel;
forming a top metallic layer on the channel layer to cover the channel; and
forming a lattice of openings in the top metallic layer, an opening of the lattice of openings penetrating through the top metallic layer and into the channel.

15. The method of claim 14 further comprises forming a another lattice of openings in the bottom metallic layer using one of:
reactive ion beam etching;
chemically assisted ion beam etching;
nanoimprint lithography;
electron-beam lithography;

x-ray lithography;
photolithography;
focused ion beam lithography; or
extreme UV lithography.

16. The method of claim 14 wherein forming the channel layer on the bottom layer comprises depositing the slab of channel layer material, the channel layer material comprising one or more of a semiconductor, an oxide of silicon, a nitride of silicon, a metal oxide, or a polymer.

17. The method of claim 14 wherein forming the channel in the channel layer comprises using one of:
reactive ion beam etching;
chemically assisted ion beam etching;
nanoimprint lithography;
electron-beam lithography;
x-ray lithography;
photolithography;
focused ion beam lithography; or
extreme UV lithography,
to remove a portion of the channel layer material corresponding to the channel prior to forming the top metallic layer.

18. The method of claim 14 wherein forming the top metallic layer on the channel layer comprises:
depositing a polymer in the channel; and
depositing the top metallic layer using chemical vapor deposition evaporation, sputtering, or atomic layer deposition.

19. The method of claim 14 further comprising filling the opening of the lattice of openings penetrating into the channel with a dielectric to further confine the material to be transmitted within the channel.

* * * * *